United States Patent [19]
Gasman et al.

[11] Patent Number: 5,369,145
[45] Date of Patent: Nov. 29, 1994

[54] DENTURE ADHESIVE

[75] Inventors: Robert C. Gasman, West Milford, N.J.; Eddie Wong, Elmhurst; Hal C. Clarke, Elmont, both of N.Y.; Hyung-kook Ahn, Bayonne, N.J.

[73] Assignee: Block Drug Company, Jersey City, N.J.

[21] Appl. No.: 76,810

[22] Filed: Jun. 14, 1993

[51] Int. Cl.$^5$ .................. A61K 6/00; C08K 3/18; C08K 3/10
[52] U.S. Cl. .................. 523/120; 524/432; 524/433; 524/436; 524/439; 524/45
[58] Field of Search ............ 523/120; 524/432, 439, 524/400, 45, 433, 436

[56] References Cited

U.S. PATENT DOCUMENTS

| | | | |
|---|---|---|---|
| 3,003,988 | 10/1961 | Germann et al. | 260/33.6 |
| 4,138,477 | 2/1979 | Gaffar | 424/52 |
| 4,758,630 | 7/1988 | Shah | 525/207 |
| 4,910,247 | 3/1990 | Haldar | 524/400 |
| 4,980,391 | 10/1990 | Kumar | 524/45 |
| 5,001,170 | 3/1991 | Keegan | 523/120 |
| 5,006,571 | 4/1991 | Kumar | 523/120 |
| 5,037,924 | 7/1991 | Tazi et al. | 526/572 |
| 5,066,710 | 3/1991 | Simonet et al. | 524/555 |
| 5,073,604 | 12/1991 | Holeva | 525/327.8 |
| 5,093,387 | 12/1991 | Schobel | 523/120 |
| 5,304,616 | 4/1994 | Rajaiaj et al. | 526/240 |

FOREIGN PATENT DOCUMENTS

| | | |
|---|---|---|
| 406643 | 6/1990 | European Pat. Off. . |
| 1492038 | 9/1974 | United Kingdom . |
| 9210986 | 7/1992 | WIPO . |
| 9210987 | 7/1992 | WIPO . |
| 9210988 | 7/1992 | WIPO . |
| 9222280 | 12/1992 | WIPO . |

OTHER PUBLICATIONS

*Journal of Dental Research*, "Zinc Polycarboxylate Cements: A Chemical Study of Erosion and Its Relationship to Molecular Structure", vol. 55, No. 2 (Mar.-Apr.) pp. 299-309 1976 (S. Crisp et al.).
Chemical Abstracts 115:51067c.
Chemical Abstracts 115:184956p.
Chemical Abstracts 115:99397n.
Chemical Abstracts 118:66628x.
"Dilatometric Studies of Counterion Binding by Polycarboxylates", *The Journal of Physical Chemistry*, vol. 76, No. 2, 1972, A. James Begala and Ulrich P. Strauss.

*Primary Examiner*—Paul R. Michl
*Assistant Examiner*—LaVonda R. DeWitt
*Attorney, Agent, or Firm*—Ostrolenk, Faber, Gerb & Soffen

[57] ABSTRACT

A denture adhesive composition contains an adhesive mixture comprising carboxymethyl cellulose and partially neutralized sodium, a salt of an alkylvinyl ether maleic acid copolymer that forms crosslinked polymer complex compounds in situ with zinc cations.

41 Claims, No Drawings

DENTURE ADHESIVE

BACKGROUND OF THE INVENTION

1. Field of the Invention

This invention relates to denture adhesives and methods of making and using denture adhesives.

2. Description of Related Art

Dentures are usually secured in the mouth using creams or powders having adhesive properties. These powders or creams serve both to adhere the dentures to the gums but also to provide a cushion and sealant between the gums and the dentures to permit a comfortable fit.

Denture adhesives must have acceptable organoleptic qualities and need to be sufficiently strong so that a daily application of the adhesive is sufficient for a full day's use. But, the adhesive must not prevent or hinder denture removal at the end of the day.

Most presently available commercial denture adhesives comprise vinyl alkyl ether/maleic acid (or anhydride) copolymers. This class of compounds was set out as a potential denture adhesive in U.S. Pat. No. 3,003,988 to Germann et al., issued Oct. 10, 1961. That patent is directed to synthetic, water sensitized, but water insoluble, materials comprising mixed, partial salts of lower alkyl vinyl ether-maleic anhydride copolymers for stabilizing dentures. The salts mentioned in the patent are a mixture of (a) calcium and (b) alkalis, including sodium, potassium and quaternary ammonium compounds, in a 1:1 to 5:1 mole ratio. The calcium and alkali materials are added to the copolymer to form the mixed salt.

Others have adopted the use of calcium in combination with alkali (especially sodium) salts of the copolymer of Germann et al. Examples of formulations using this combination are: U.S. Pat. No. 4,980,391 to Kumar et al., issued Dec. 25, 1990; U.S. Pat. No. 5,037,924 to Tazi et al.; and U.S. Pat. No. 4,910,247 to Haldar et al., issued Mar. 20, 1990. European Patent Application No 406,643, filed Jun. 22, 1990, is directed to aluminum, calcium and sodium salts of a lower alkyl vinyl ether/maleic acid copolymer.

These salts, however, have not proven to be fully effective at securing the denture and are susceptible to "washout," the erosion of the adhesive from under the denture during use. As a result, these formulations provided less than the twelve hours of holding power that denture wearers have begun to demand.

In order to provide additional adhesive and cohesive properties, others have turned to zinc and strontium salts. Examples of these salts are found in, for example, PCT application No. WO 92/22280, published Dec. 23, 1992, assigned to Richardson-Vicks, Inc. (the cations may also include calcium cations, sodium cations or both); U.S. Pat. No. 4,758,630 to Shah et al., issued Jul. 19, 1988 (zinc partial salts or strontium partial salts); U.S. Pat. No. 5,073,604 to Holeva et al., issued Dec. 17, 1991 (partial calcium salts in combination with either partial zinc or partial strontium salts); PCT application No. WO 92/10988, published Jul. 9, 1992, assigned to Richardson-Vicks, Inc. (the salts may comprise zinc, strontium, sodium, calcium, magnesium, potassium or ammonium cations and mixtures thereof); and PCT Application No. WO 92/10987, published Jul. 9, 1992, assigned to Richardson-Vicks, Inc. (the salts may include zinc or strontium in combination with sodium and calcium cations).

Moreover, PCT Application No. WO 92/10986 is directed to mixed partial salts of lower alkyl vinyl ether-maleic anhydride copolymers. The salts are zinc or strontium cations with calcium cations.

Salts of vinyl alkyl ether/maleic acid copolymers have also found use outside the denture adhesive field. U.K. Patent Specification No. 1,492,038 filed Sept. 19, 1974, assigned to Smith & Nephew Research, Ltd., is directed to orthopedic bandages comprising a vinyl alkyl ether/maleic anhydride copolymer with zinc, aluminum or magnesium oxides. U.S. Pat. No. 4,138,477 to Gaffar, issued Feb. 6, 1979, is directed to mouth odor control using zinc salts of vinyl alkyl ether/maleic anhydride copolymers. Begala, A. & Strauss, U., "Dilatometric Studies of Counterion Binding by Polycarboxylates," J. Phys. Chem., 76, p 254–60 (1972), investigates the volume changes associated with bonding of hydrogen and magnesium ions to, inter alia, a vinyl methyl ether/maleic anhydride copolymer. And Crisp, S, et al., "Zinc Polycarboxylate Cements: A Chemical Study of Erosion and Its Relationship to Molecular Structure," J. Dental Rsch., 55(2), p. 299–308 (1976), reports on magnesium or zinc salts of lower alkyl vinyl ether/maleic acid copolymers.

Despite the effort put into improving the properties of the copolymer and the salts derived from the copolymers, these formulations do not provide the full measure of adhesion, cohesion, and resistance to washout from beneath the denture necessary for a completely successful product.

SUMMARY OF THE INVENTION

The principal object of the present invention therefore is to provide a denture adhesive composition having both strong adhesive properties and good washout resistance to provide long holding properties. The denture adhesive must exhibit sufficient tack initially upon contact with oral mucosa and build up cohesive strength quickly when hydrated with moisture or saliva and be able to resist stresses such as those that occur upon mastication. The denture adhesive must retain its adhesive properties for prolonged periods of time.

Another object of the invention is to provide a method for making the denture adhesive composition to achieve in situ zinc bonding.

Still another object of the invention is to provide a method for using the denture adhesive to secure dentures in the mouth.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides a denture adhesive composition comprising: (a) a salt of a vinyl alkyl ether/maleic anyhdride or acid copolymer and a cation from Group I or Group II of the Periodic Table; and (b) a zinc compound, nonionically associated with the salt.

To further achieve the foregoing objects and in accordance with the purpose of the invention, the invention further provides a method for making a denture adhesive compound comprising the steps of: (a) preparing a salt of a vinyl alkyl ether/maleic anhydride or acid copolymer with a cation from Group I or Group II of the Periodic Table; (b) combining the salt with a zinc compound in a nonionic manner in a suitable carrier material to form the denture adhesive compound.

To further achieve the foregoing objects and in accordance with the purpose of the invention, as embodied and broadly described herein, the invention provides a method for adhering dentures to gums comprising the steps of: (a) treating the dentures with a denture adhesive composition comprising: (i) a salt of a vinyl alkyl ether/maleic anhydride or acid copolymer and a cation from Group I or Group II of the Periodic Table; and (ii) a zinc compound, nonionically associated with the salt; and (b) placing the dentures in close proximity to gum tissue thereby engaging the denture adhesive composition.

DESCRIPTION OF THE PREFERRED EMBODIMENTS

Reference will now be made in detail to the presently preferred embodiments of the invention.

The denture adhesive composition of the invention is most suitable in liquid and cream forms. The composition preferably contains both active and nonactive ingredients.

The active ingredients are cations, alkyl vinyl ether/maleic anhydride copolymer salts, preferably with 70–40% unreacted carboxylic acid groups, carboxyl methyl cellulose gum, zinc oxide and/or zinc salts (organic or inorganic salts).

The copolymer of the invention is a vinyl alkyl ether/maleic acid or anhydride copolymer. The preferred copolymer is a copolymer available from GAF sorporation, Wayne, N.J., under the trademark "GANTREZ" in two forms: the acid form is sold under the trademark GANTREZ S" Series, and the preferred type of acid is identified as "GANTREZ S95" or "GANTREZ S97." The anhydride form is sold as the "GANTREZ AN" Series, and the preferred anhydride is "GANTREZ AN169."

The preferred alkali cations are alkali cations, although cations from Group I and Group II of the Periodic Table may be selected. Acceptable cations include sodium, potassium, magnesium, calcium, and strontium. Preferred are sodium and potassium, and most preferred is sodium.

When the salt is prepared, the cations associate with ionic bonding sites on the copolymer and are neutralized. Preferably less than all the ionic bonding sites on the copolymer are used. More preferably, the cations occupy from about 5% to about 60%, and most preferably from about 20% to about 60% of the bonding sites on the copolymer, leading to a "partially neutralized" copolymer. 40% partial neutralization is most preferred.

Preferably, the salt comprises from about 10% to about 50% by weight of the total denture adhesive composition. More preferably the salt comprises from about 20% to about 40% of the final denture adhesive composition and most preferably about 30% by weight of the denture adhesive composition.

Carboxymethyl cellulose gum is used for sensitizing the adhesive to moisture, enhancing the cohesive properties of the formulation and improving gel strength. Acceptable substitutes may be selected from carboxyethyl cellulose and carboxypropyl cellulose materials.

The carboxymethyl cellulose gum preferably comprises from about 10% to about 30% by weight of the denture adhesive composition, more preferably from about 15% to about 25% and most preferably about 20% of the composition. The carboxymethyl cellulose may be present in the form of a full or partial salt, preferably a sodium salt. During use, zinc from the added salt of the invention will replace at least some of the sodium and from crosslinks in the carboxymethyl cellulose or crosslinks with the copolymer.

Acceptable zinc compounds include oxides, carbonates and halides. While other anions of Group VI of the Periodic Table may be used in place of oxides, oxides are preferred for their ease of handling and organoleptic qualities. Preferred halides include fluorides, chlorides and bromides. Chlorides are most preferred.

Nonactive ingredients present in the denture adhesive include thickening agents and carriers, such as petrolatum and mineral oil, flavors, colors, preservatives, thickeners and non-toxic anticaking agents such as silica, magnesium stearate and talc. Acceptable nonactive ingredients, and the appropriate levels at which the ingredients should be present in a particular formulation for a specific purpose are well known in the art.

For a cream base, the mineral oil or other carrier preferably comprises from about 10% to about 30% by weight of the denture adhesive, preferably from about 15% to about 25% by weight. Petrolatum or some other thickening agent comprises from about 15% to about 30% by weight of the denture adhesive composition, preferably from about 20% to about 30% by weight.

Other nonactive ingredients comprise colorants, flavors and preservatives and may comprise up to about 10% by weight of the denture adhesive composition.

In use, the partially neutralized copolymer salt will provide the initial tack quickly when it comes in contact with moisture in the oral mucosa. When it is hydrated with moisture or saliva, zinc oxide and/or the other zinc salts present in the oil phase of the adhesive become available to form zinc copolymer complexes. Zinc from zinc oxide will react more favorably with acidic carboxylic acid groups by means of an acid-base interaction while the zinc from zinc halide salts would be more effective in replacing sodium cations from carboxylate groups.

The method of making the denture adhesive composition is a two-step process of making the copolymer salt and then incorporating the salt into the denture adhesive composition.

The copolymer salt is made by heating a suitable solvent, such as water (deionized or distilled water is preferable) to a temperature sufficient to hasten dissolution of the copolymer in the solvent. In the case of methyl vinyl ether/maleic anhydride copolymer being dissolved in water, the temperature is about 90° C.

Separately, a donor solution for the cation can be prepared. Preferably the solvent for the solution is identical to, or compatible with, the solvent for the copolymer. Preferably the donor solution comprises the cation or cations to be used to form the salt and an initiator, such as a Lewis acid or base, to facilitate the partial substitution of the cation for the hydrogen in the copolymer. In the event that the cation is sodium or potassium, suitable solutions would include solutions of sodium or potassium hydroxide, compounds that provide both the cation and a Lewis base.

After the copolymer solution has cooled sufficiently, the cation donor solution and the copolymer solution are allowed to react. The product is dried in a drier to form a dried material that is then milled to a small size (about 100 mesh) and further processed to form the denture adhesive of the invention using techniques well known in the art.

The following non-limiting examples will serve to illustrate the invention.

EXAMPLE 1

3.25 Kg of purified water were heated in a reaction vessel equipped with a high speed stirrer to 90° C. 260 grams of methyl vinyl ether/maleic anhydride copolymer were slowly added to the reaction vessel and mixing was continued until a clear solution was obtained. The solution was then cooled to 65°–75° C.

7.41% (by weight) NaOH solution was prepared in a separate container. When the temperature of the copolymer solution reached 65°–75° C., 539.8 grams of 7.41% NaOH solution was added while mixing at high speed (to prevent localized reaction).

The combination was then mixed for 15 minutes after the addition of the NaOH solution. The sodium salt of methyl vinyl ether/maleic anhydride copolymer was then transferred to a series of shallow steel drying trays, and the trays were placed in a hot air convection oven at 75° C. for 18–20 hours. The dried sodium salt was then milled through a suitable mill. The milled salt is then screened through a 100 mesh sieve. The powder had a bulk density of about 0.5–0.9 g/cc and the pH of one percent solution is 4–5. This salt was identified as a 30% Na partial salt of MVE/MA copolymer.

EXAMPLE 2

3.25 kg purified water was heated in a reaction vessel equipped with a high speed stirrer to 90° C. 248.9 g methyl vinyl ether/maleic anhydride copolymer was slowly added to the reaction vessel, and mixing was continued until a clear solution was obtained. The heat was then turned off and the solution was cooled to 65°–75° C.

In a separate container, a 9.26% NaOH solution was prepared. 551.1 g of the NaOH solution were slowly added to the cooled solution while mixing. Mixing was continued for 15 minutes.

The sodium salt/copolymer solution was then transferred to shallow stainless steel drying trays and placed in a hot air convection oven at 75° C. for 18–20 hours. The dried sodium Gantrez salt was then milled through a suitable mill. The milled salt is then screened through a 100 mesh sieve. The powder had a bulk density of about 0.5 to 0.9 g/cc, and the pH of a one percent solution was 4–6. The salt was a 40% Na partial salt of MVE/MA copolymer.

EXAMPLE 3

3.25 kg purified water was heated in a reaction vessel equipped with a high speed stirrer to 90° C. 238.8 g methyl vinyl ether/maleic anhydride copolymer was slowly added to the reaction vessel and mixing was continued until a clear solution was obtained. The heat was then turned off and the solution was cooled to 65°–75° C. In a separate container, a 10.91% NaOH solution was prepared. 561.2 g of the NaOH solution were slowly added to the cooled solution while mixing. Mixing was continued for 15 minutes.

The sodium salt/copolymer solution was then transferred to shallow stainless steel drying trays and placed in a hot air convection oven at 75° C. for 18–20 hours. The dried sodium salt is then milled through a suitable mill. The milled salt is then screened through a 100 mesh sieve. The powder would have a bulk density of about 0.5 to 0.9 g/cc, and the pH of a one percent solution is 5–7. The salt is a 50% Na partial salt of MVE/MA copolymer.

EXAMPLE 4

3.25 kg purified water was heated in a reaction vessel equipped with a high speed stirrer to 90° C. 229.4 g methyl vinyl ether/maleic anhydride copolymer was slowly added to the reaction vessel and mixing was continued until a clear solution was obtained. The heat was then turned off and the solution was cooled to 65°–75° C. In a separate container, a 12.37% NaOH solution was prepared. 570.4 g of the NaOH solution were slowly added to the cooled solution while mixing. Mixing was continued for 15 minutes.

The sodium salt/copolymer solution was then transferred to shallow stainless steel drying trays and placed in a hot air convection oven at 75° C. for 18–20 hours. The dried sodium salt is then milled through a suitable mill. The milled salt is then screened through a 100 mesh sieve. The powder would have a bulk density of about 0.5 to 0.9 g/cc, and the pH of a one percent solution is 6–8. The salt is a 60% Na partial salt of MVE/MA copolymer.

EXAMPLE 5

Denture adhesive creams were prepared using the sodium salts of Examples 1–4. The respective salts were blended with the other ingredients in Table 1 in the following manner.

Mineral Oil was heated to a temperature of about 165° F. Petrolatum of about the same temperature was added to the mineral oil and blended until a uniform consistency was reached. Sodium carboxymethyl cellulose (CMC), colorant, zinc oxide, zinc chloride and flavoring were added to the mixture, as appropriate, while the mixture slowly cooled to about 120° F. The respective salts were added at about 120° F. The combination was then cooled to room temperature and tested for shear strength.

The shear strength was measured as follows: three homogeneously mixed samples of adhesive/water combinations were prepared at weight ratios of 1:1, 1:0.75 and 1:0.5. Each combination was spread on about 1 square inch of a separate transparent acrylic slide. A second slide with a ⅜" diameter hole in one end was placed over the first slide. 20 lbs. pressure was placed on the slide and was held at that level for 5 seconds. The slides were set aside for hydration for about 1 or about 5 minutes.

20 lbs. pressure was again applied for 5 seconds, and the shear strength was measured on an Instron Model 1122 machine. The results of the measurements were averaged. The results at 1 minute and at 5 minutes hydration are reported in Table 1.

EXAMPLE 6

As a comparison to Example 5, commercial denture adhesives were tested for shear strength. The results are shown in Table 2.

TABLE 1

| Ingredient | Test Formulation Number | | | | | |
| --- | --- | --- | --- | --- | --- | --- |
| | 1 | 2 | 3 | 4 | 5 | 6 |
| Mineral Oil | 23.0 | 19.0 | 16.5 | 16.5 | 16.5 | 20.0 |

TABLE 1-continued

| Ingredient | Test Formulation Number | | | | | |
|---|---|---|---|---|---|---|
| | 1 | 2 | 3 | 4 | 5 | 6 |
| Petrolatum | 22.0 | 26.0 | 27.0 | 27.0 | 28.0 | 26.0 |
| Colorant | 0.05 | 0.05 | 0.05 | 0.05 | 0.05 | 0.05 |
| CMC (sodium) | 19.0 | 19.0 | 20.0 | 20.0 | 19.0 | 19.0 |
| 30% Na Gantrez Salt | 29.5 | — | — | — | — | — |
| 40% Na Gantrez Salt | — | 29.5 | — | — | 30.0 | 29.5 |
| 50% Na Gantrez Salt | — | — | 30.0 | — | — | — |
| 60% Na Gantrez Salt | — | — | — | 30.0 | — | — |
| Zinc Oxide | 6.0 | 6.0 | 6.0 | 6.0 | 3.0 | 5.0 |
| Zinc Chloride | — | — | — | — | 3.0 | — |
| Preservative | 0.05 | 0.05 | 0.05 | 0.05 | 0.05 | 0.05 |
| Flavor | 0.4 | 0.4 | 0.4 | 0.4 | 0.4 | 0.4 |
| Shear (1 minute) g/in$^2$ | 715 | 953 | 1180 | 1816 | 1135 | 1249 |
| Shear (5 minutes) g/in$^2$ | 1498 | 2088 | 2361 | 2542 | 1385 | 2043 |

TABLE 2

| Shear Rate | Commercial Formulation U.S. Pat. No. 3,003,988 | Commercial Formulation U.S. Pat. Nos. 4,758,630 5,073,604 |
|---|---|---|
| Shear (1 minute) g/in$^2$ | 397 | 1158 |
| Shear (5 minutes) g/in$^2$ | 658 | 1271 |

The purpose of the above description is to illustrate some embodiments of the present invention without implying a limitation. It will apparent to those skilled in the art that various modifications and variations may be made in the apparatus or procedure of the invention without departing from the scope or spirit of the invention.

What is claimed is:

1. A denture adhesive composition comprising:
   (a) a salt comprising (i) a copolymer of (A) a vinyl alkyl ether and (B) maleic anhydride or maleic acid copolymer and (ii) a cation from Group IA or Group IIA of the Periodic Table; and
   (b) a zinc compound, nonionically associated with said salt.

2. The denture adhesive of claim 1, wherein said cation is selected from the group consisting of: sodium, potassium, magnesium, calcium, and strontium cations.

3. The denture adhesive of claim 2, wherein said cation is selected from the group consisting of sodium and potassium.

4. The denture adhesive of claim 1, wherein the copolymer is an alkali metal salt of methyl vinyl ether-co-maleic acid.

5. The denture adhesive of claim 1, wherein the copolymer is partially neutralized.

6. The denture adhesive of claim 5, wherein the copolymer is from about 5% to about 60% neutralized.

7. The denture adhesive of claim 6, wherein the copolymer is from about 20% to about 60% neutralized.

8. The denture adhesive of claim 1, wherein said salt comprises from about 20% to about 50% by weight of the total denture adhesive composition.

9. The denture adhesive of claim 8, wherein the salt comprises from about 25% to about 40% of the denture adhesive composition.

10. The denture adhesive of claim 9, wherein the salt comprises about 30% by weight of the denture adhesive.

11. The denture adhesive of claim 1, further comprising carboxy methyl cellulose gum.

12. The denture adhesive of claim 11, wherein said carboxy methyl cellulose gum comprises from about 10% to about 30% by weight of the denture adhesive.

13. The denture adhesive of claim 12, wherein said carboxy methyl cellulose gum comprises from about 15% to about 25% by weight of the denture adhesive.

14. The denture adhesive of claim 13, wherein said carboxy methyl cellulose gum comprises about 20% by weight of the composition.

15. The denture adhesive of claim 1, wherein said zinc compound is selected from the group consisting of oxides and halides.

16. The denture adhesive of claim 15, wherein said zinc compound is selected from the group consisting of fluorides, chlorides and bromides.

17. The denture adhesive of claim 16, wherein said zinc compound is zinc chloride.

18. A denture adhesive comprising a mixture of (a) a partially neutralized sodium salt of a copolymer of an alkyl vinyl ether and maleic anhydride or maleic acid and (b) a compound selected from the group consisting of zinc oxide, zinc carbonate, zinc chloride, zinc fluoride and zinc bromide.

19. A method for making a denture adhesive comprising the steps of: (a) preparing a salt of a vinyl alkyl ether/maleic anhydride or acid copolymer with a cation from Group IA or Group IIA of the Periodic Table; and (b) combining the salt with a zinc compound in a nonionic manner to form the denture adhesive compound.

20. The method of claim 19 wherein said copolymer comprises maleic anhydride.

21. The method of claim 19, wherein said copolymer comprises maleic acid.

22. The method of claim 19, wherein said cation is selected from the group consisting of: sodium, potassium, magnesium, calcium, and strontium cations.

23. The method of claim 22, wherein said cation is selected from the group consisting of sodium and potassium.

24. The method of claim 23, wherein said cation is sodium.

25. The method of claim 19, wherein the copolymer comprises methyl vinyl ether.

26. The method of claim 19, wherein the copolymer is partially neutralized.

27. The method of claim 26, wherein the copolymer is from about 5% to about 60% neutralized.

28. The method of claim 27, wherein the copolymer is from about 20% to about 60% neutralized.

29. The method of claim 19, wherein said salt comprises from about 20% to about 50% by weight of the total denture adhesive composition.

30. The method of claim 29, wherein the salt comprises from about 25% to about 40% of the denture adhesive composition.

31. The method of claim 30, wherein the salt comprises about 30% by weight of the denture adhesive.

32. The method of claim 19, further comprising carboxy methyl cellulose gum.

33. The method of claim 32, wherein said carboxy methyl cellulose gum comprises from about 5% to about 55% by weight of the denture adhesive.

34. The method of claim 33, wherein said carboxy methyl cellulose gum comprises from about 15% to about 25% by weight of the denture adhesive.

35. The method of claim 34, wherein said carboxy methyl cellulose gum comprises about 20% by weight of the composition.

36. The method of claim 23, wherein said zinc compound is selected from the group consisting of oxides and halides.

37. The method of claim 36, wherein said zinc compound is selected from the group consisting of fluorides, chlorides and bromides.

38. The method of claim 37, wherein said zinc compound is zinc chloride.

39. A method for adhering dentures to gums comprising the steps of: (a) treating the dentures with a denture adhesive composition comprising: (i) a salt of a vinyl alkyl ether/maleic anhydride or acid copolymer and a cation from Group IA or Group IIA of the Periodic Table; and (ii) a zinc compound, nonionically associated with the salt; and (b) placing the dentures in close proximity to gum tissue thereby engaging the denture adhesive composition.

40. The method of claim 39, wherein said salt comprises a partially neutralized sodium salt of a methyl vinyl ether/maleic anhydride copolymer.

41. The method of claim 39, wherein said zinc compound is selected from the group consisting of zinc oxide and zinc chloride.

* * * * *